(12) United States Patent
Shah et al.

(10) Patent No.: US 12,350,046 B2
(45) Date of Patent: Jul. 8, 2025

(54) ANALYTE SENSOR

(71) Applicant: PercuSense, Inc., Valencia, CA (US)

(72) Inventors: Rajiv Shah, Rancho Palos Verdes, CA (US); Bradley C Liang, Bloomfield Hills, MI (US); Katherine Wolfe, Dunwoody, GA (US)

(73) Assignee: PercuSense, Inc., Valencia, CA (US)

( * ) Notice: Subject to any disclaimer, the term of this patent is extended or adjusted under 35 U.S.C. 154(b) by 438 days.

(21) Appl. No.: 17/871,718

(22) Filed: Jul. 22, 2022

(65) Prior Publication Data

US 2024/0023847 A1    Jan. 25, 2024

(51) Int. Cl.
  *G01N 27/327* (2006.01)
  *A61B 5/145* (2006.01)
  *A61B 5/1486* (2006.01)
  *A61B 5/1495* (2006.01)
  *C12Q 1/00* (2006.01)

(52) U.S. Cl.
  CPC ...... *A61B 5/14865* (2013.01); *A61B 5/14532* (2013.01); *A61B 5/1495* (2013.01); *C12Q 1/005* (2013.01); *C12Q 1/006* (2013.01); *G01N 27/3272* (2013.01); *A61B 2562/0295* (2013.01)

(58) Field of Classification Search
  CPC ............ G01N 27/308; G01N 27/3272; G01N 27/327; G01N 27/3271; A61B 5/1486; A61B 5/14532; C12Q 1/006
  See application file for complete search history.

(56) References Cited

U.S. PATENT DOCUMENTS

2007/0131549 A1*  6/2007  Cai ..................... C12Q 1/006
                                                     204/403.02
2017/0328857 A1* 11/2017  Shah .................. G01N 27/3272

* cited by examiner

*Primary Examiner* — Gurpreet Kaur
(74) *Attorney, Agent, or Firm* — PercuSense, Inc.

(57) ABSTRACT

In one embodiment, a sensor is disclosed that includes a first conductive substrate coupled to, and electrically isolated from, a second conductive substrate. The sensor includes a first electrode trace within the first conductive substrate with a plurality of first working electrode openings. The sensor also includes a second electrode trace within the first conductive substrate with a plurality of second working electrode openings. Additionally a first transport material is included that covers the plurality of first working electrode openings and a second transport material that covers the plurality of second working electrode openings. A third transport material covers, and forms a barrier between the first and the second transport material. The sensor additionally includes a counter-reference electrode that is formed on the second conductive substrate.

10 Claims, 7 Drawing Sheets

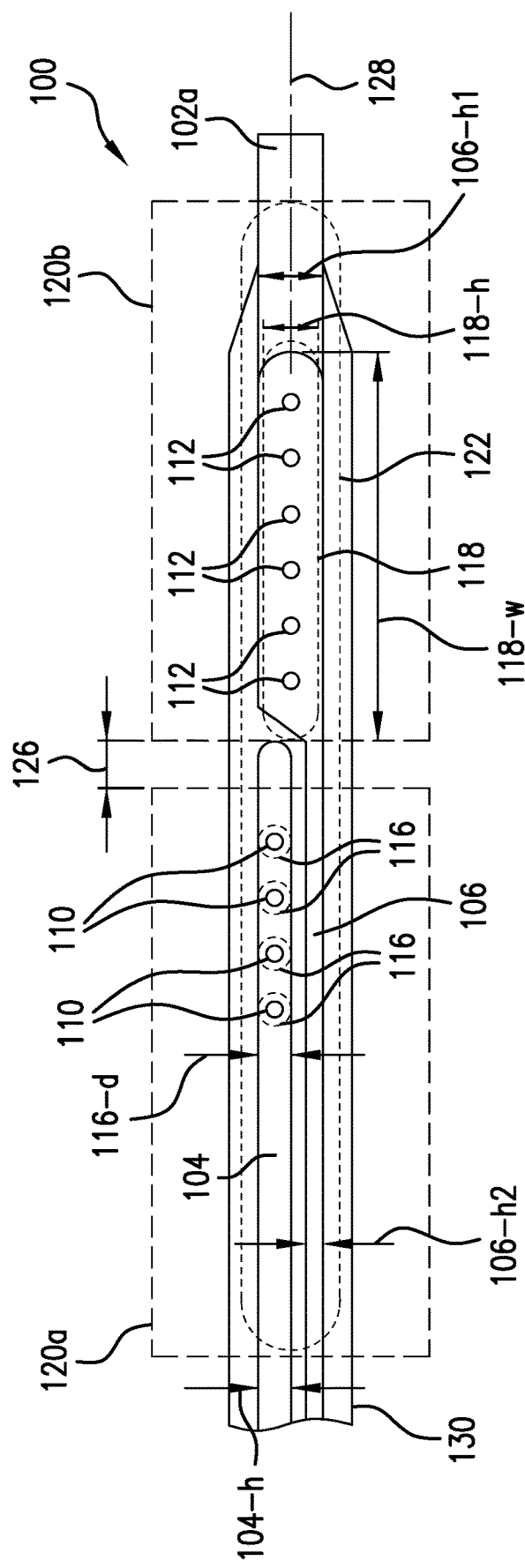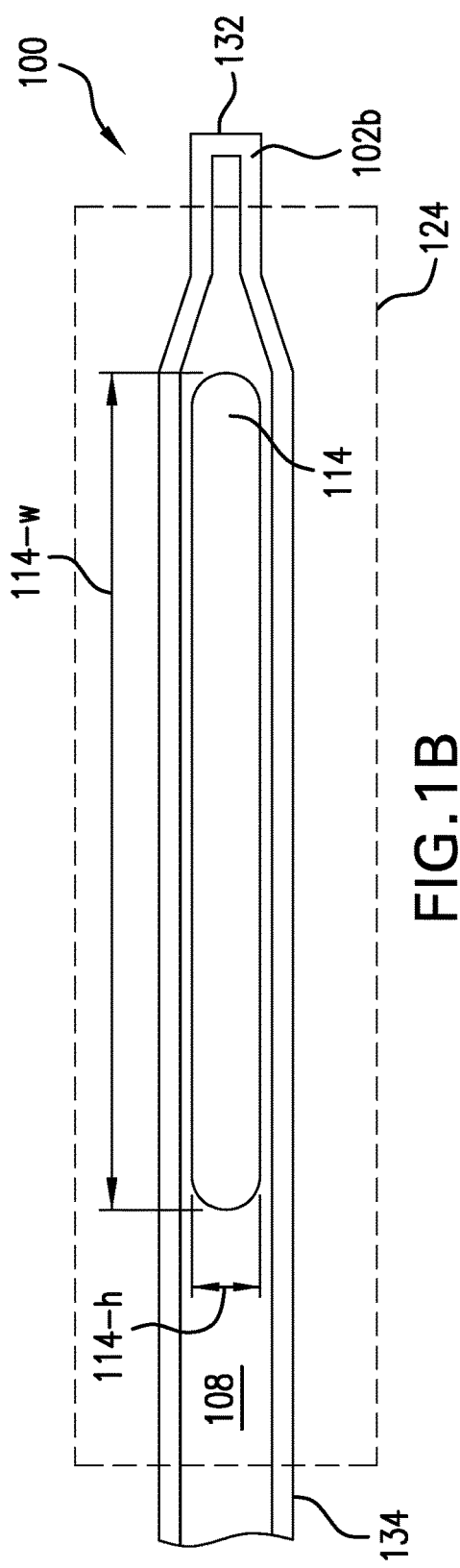
FIG.1A
FIG.1B

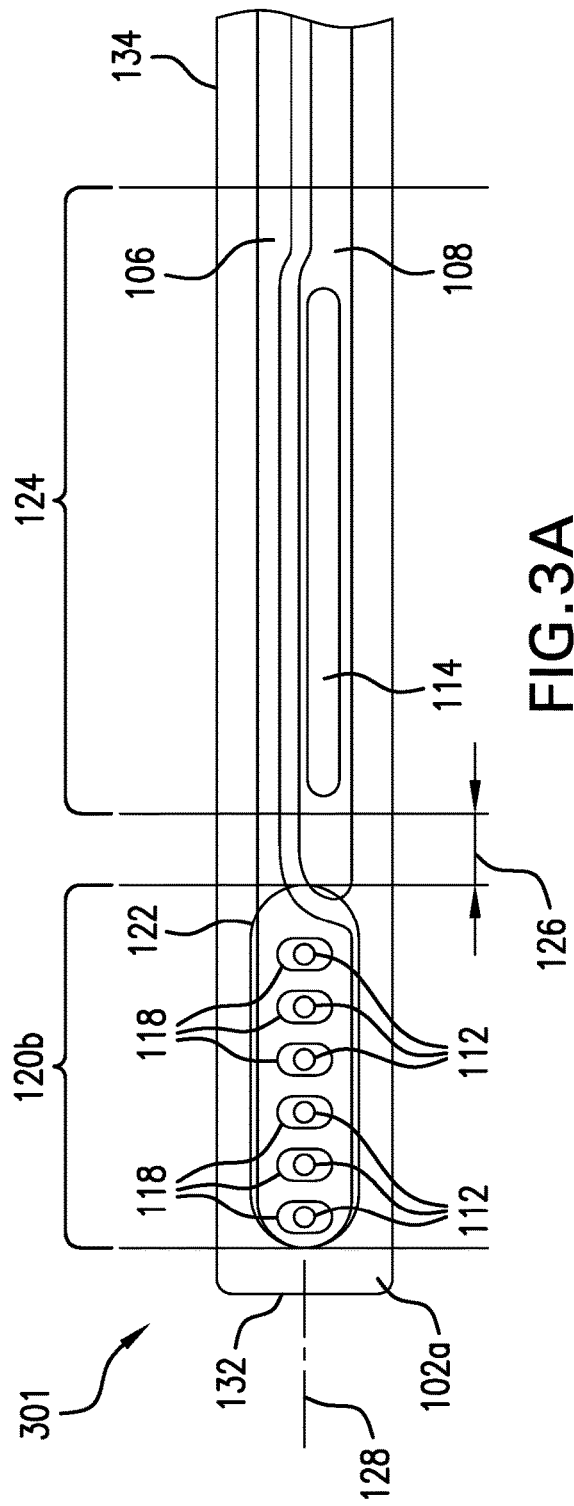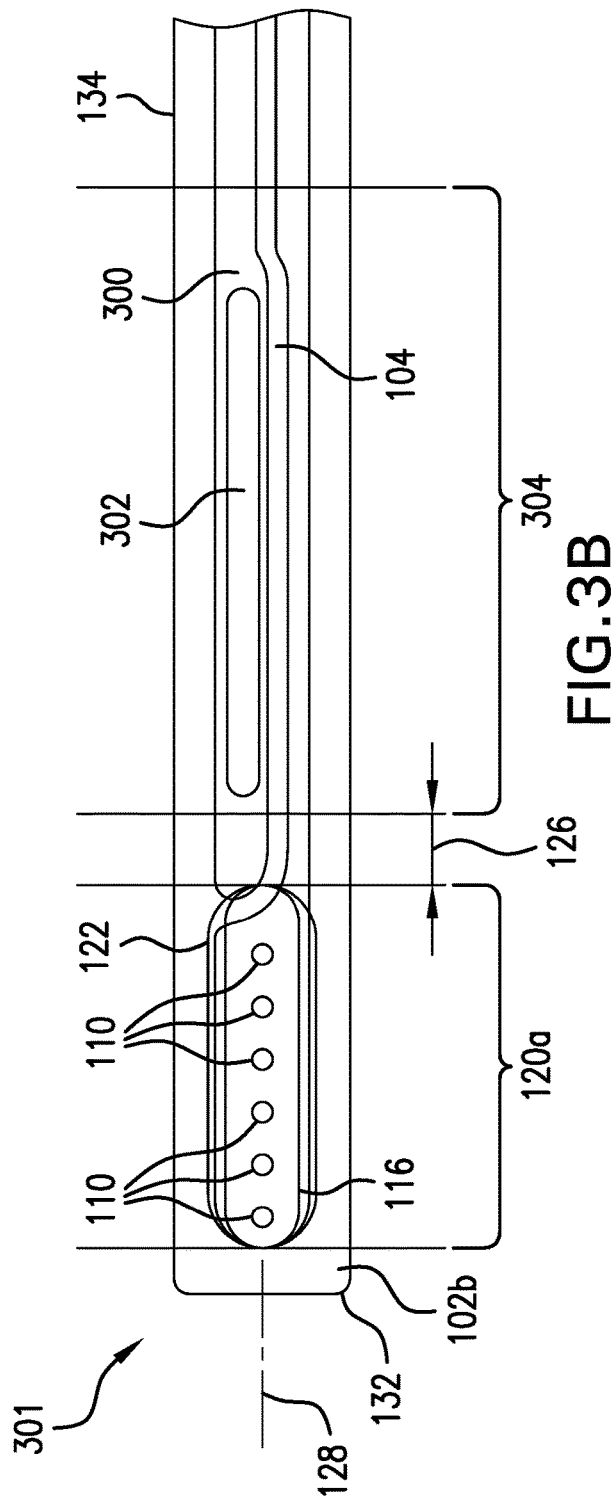

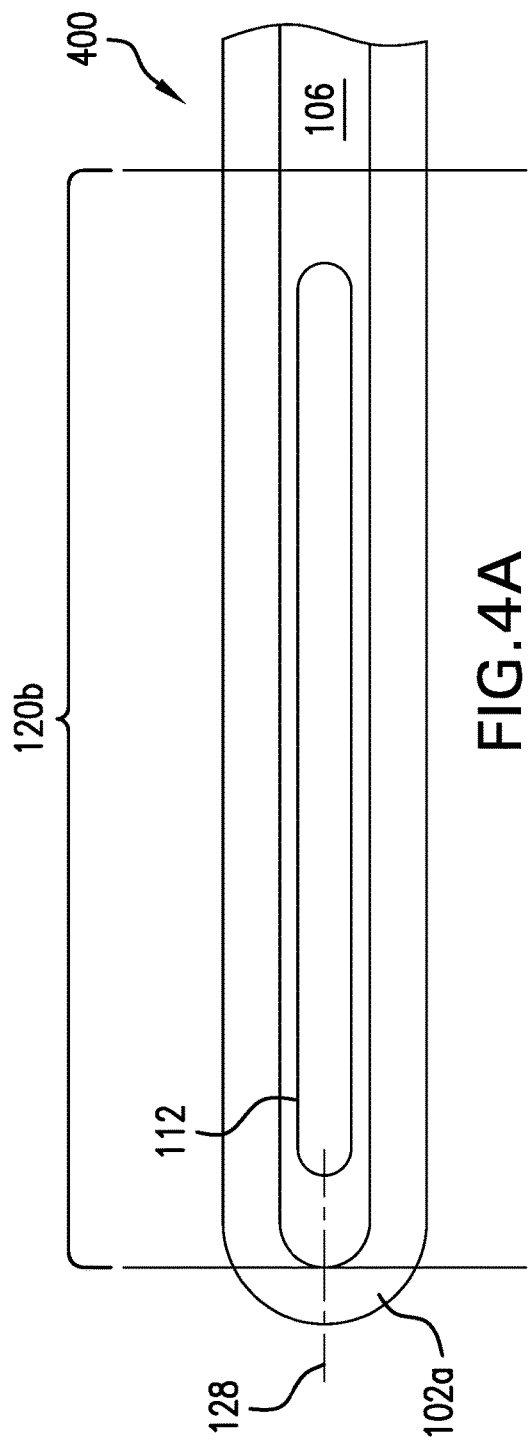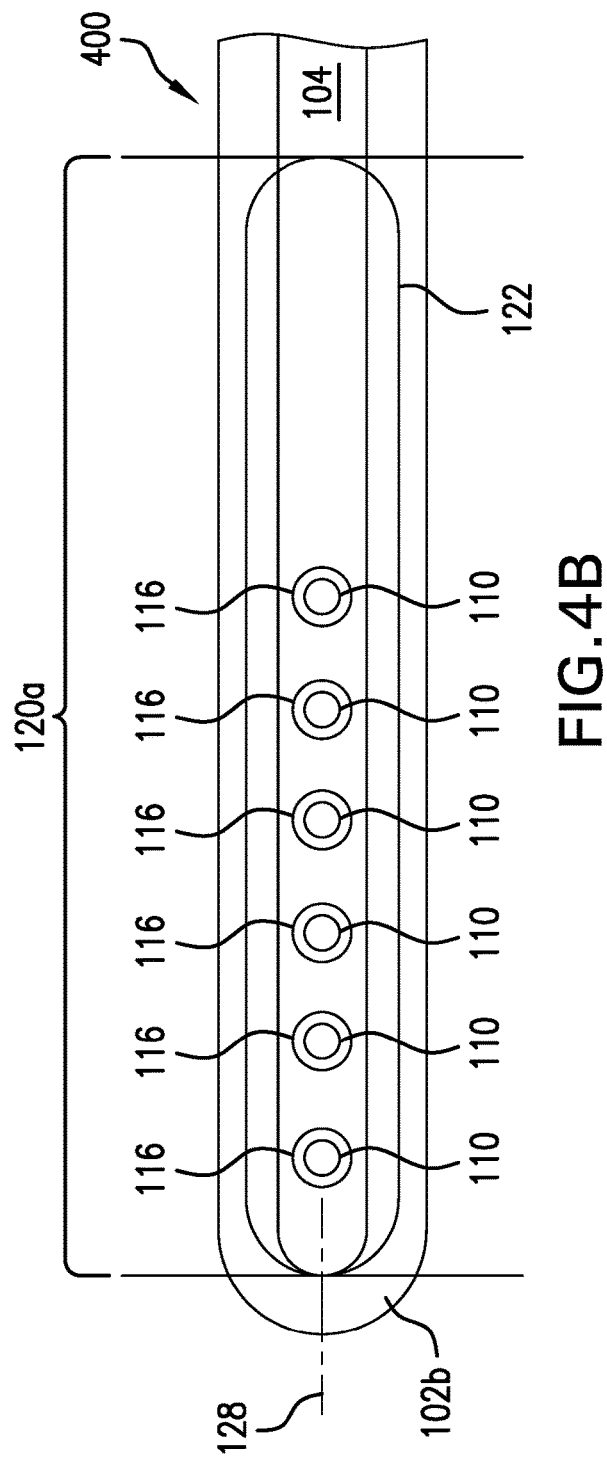
FIG.4A
FIG.4B

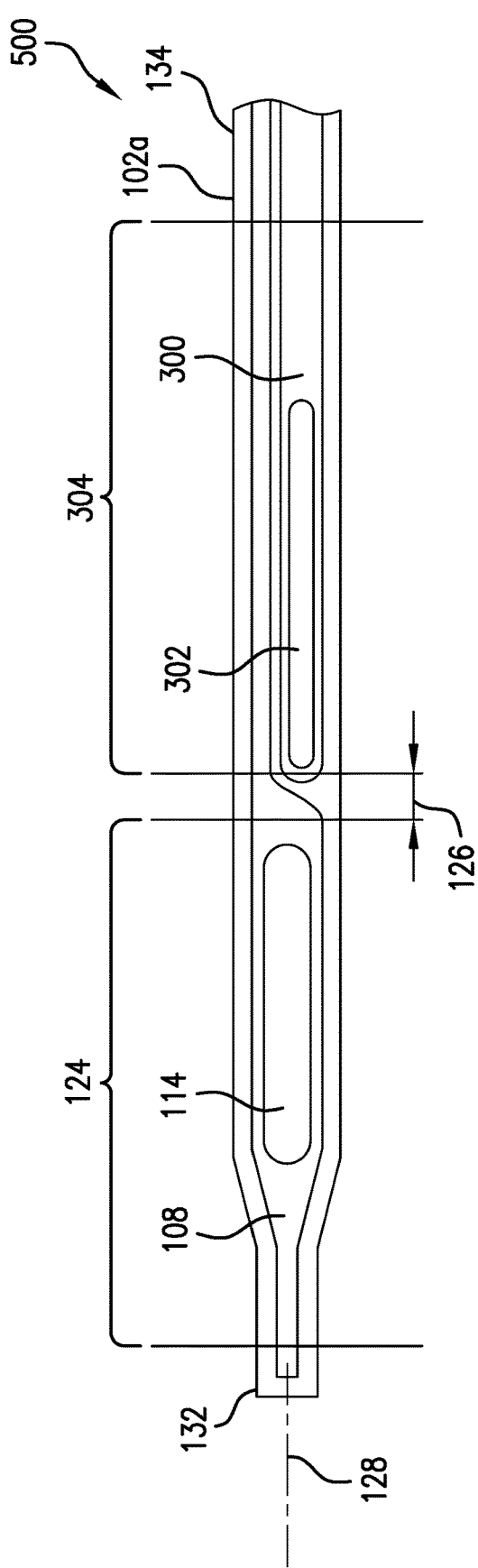
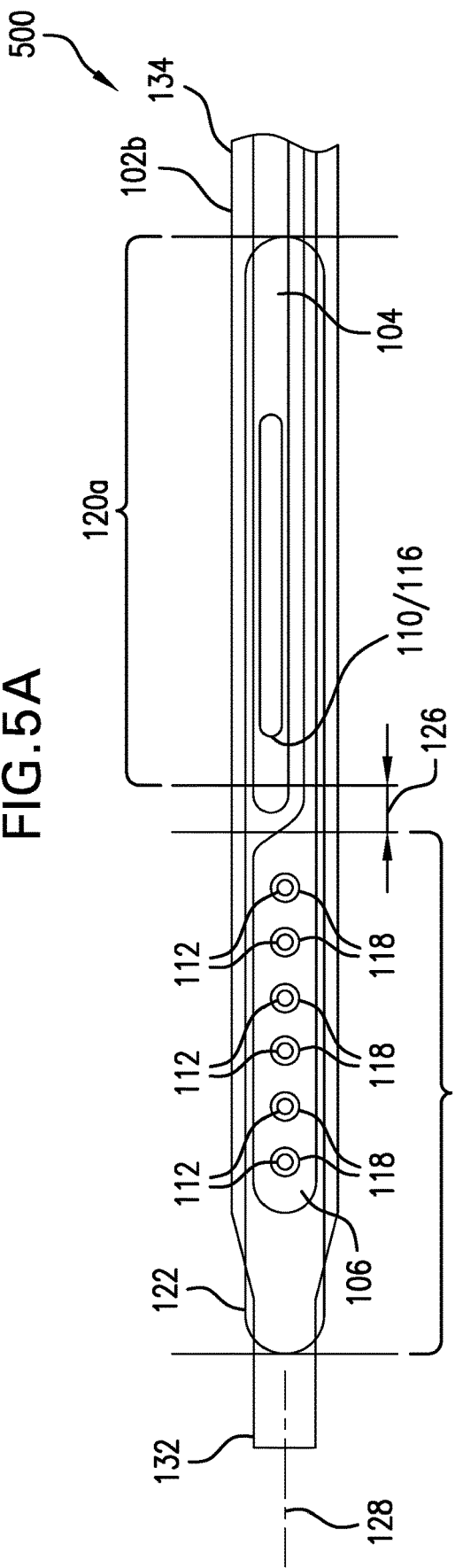
FIG.5A
FIG.5B

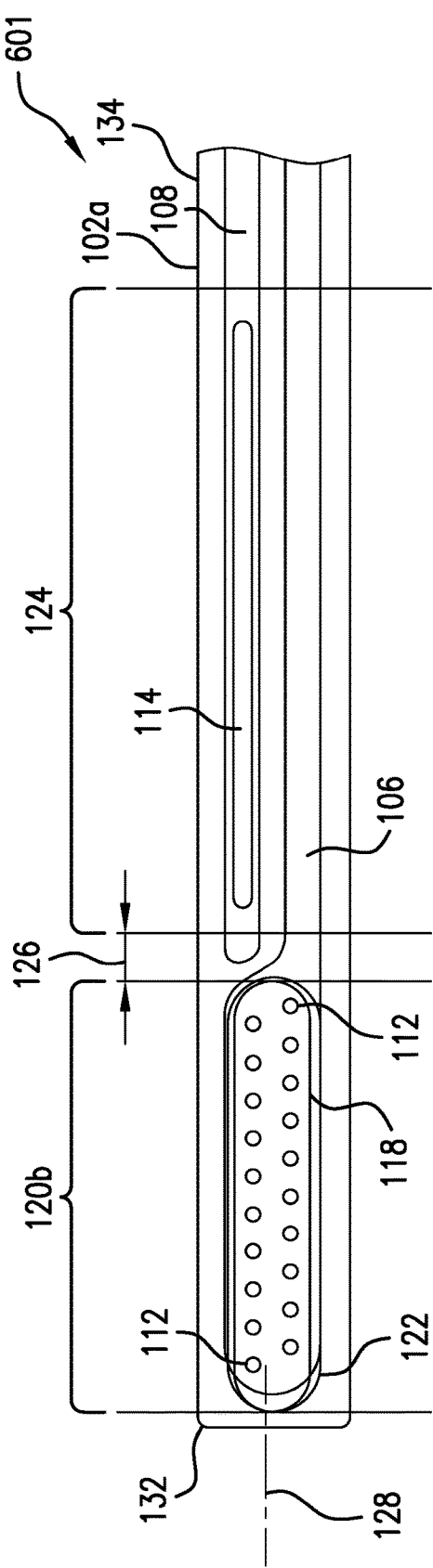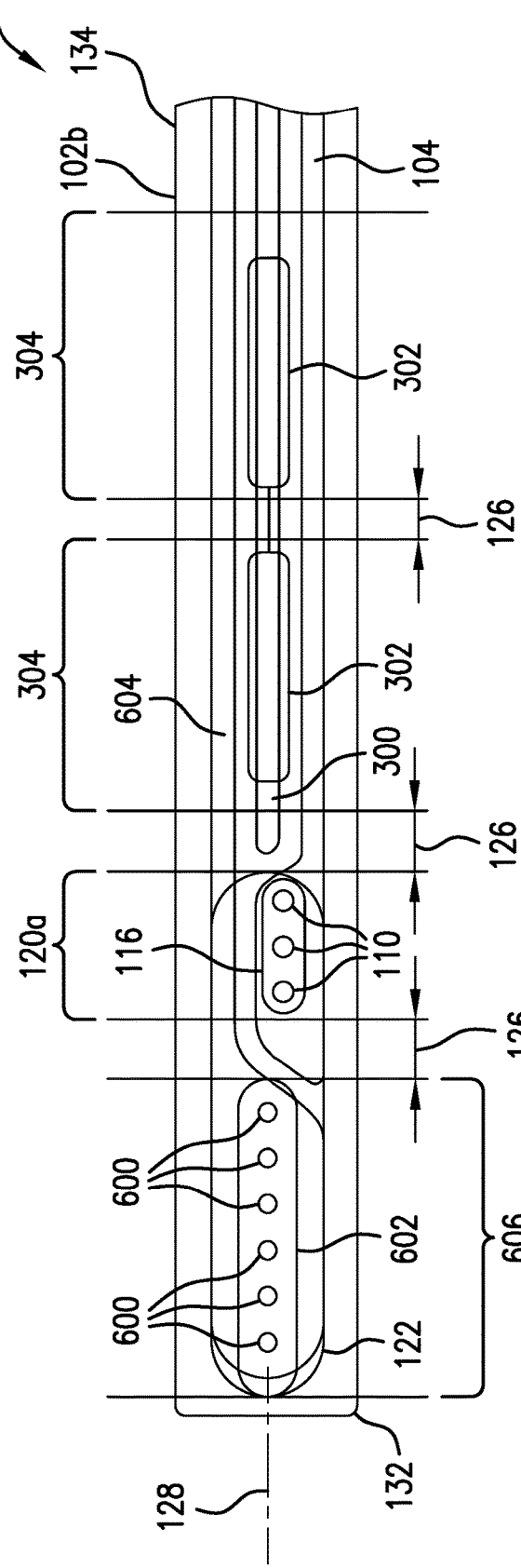
FIG. 6A
FIG. 6B

ANALYTE SENSOR

FIELD OF THE INVENTION

The present invention is generally directed to devices and methods that perform in vivo monitoring of an analyte or analytes such as, but not limited to, glucose or lactate. In particular, the devices and methods are for electrochemical sensors that provide information regarding the presence or amount of an analyte or analytes within a subject.

BACKGROUND OF THE INVENTION

In vivo monitoring of particular analytes can be critically important to short-term and long-term well being. For example, the monitoring of glucose can be particularly important for people with diabetes in order to determine insulin or glucose requirements. In another example, the monitoring of lactate in postoperative patients can provide critical information regarding the detection and treatment of sepsis.

The need to perform continuous or near continuous analyte monitoring has resulted in the development of a variety of devices and methods. Some methods place electrochemical sensor devices designed to detect the desired analyte in blood vessels while other methods place the devices in subcutaneous or interstitial fluid. Both placement locations can provide challenges to receiving consistently valid data. Furthermore, achieving consistent placement location can be critical to hydrating, conditioning and calibrating the device before actual use. Hydrating and conditioning of commercially available sensor devices can be a time consuming process often taking fractions of hours up to multiple hours. Assuming the hydrating and conditioning process is completed successfully, a user may have to compromise their freedom of movement or range of movement in order to keep the sensor properly located within their body.

Glucose sensors are one example of in vivo continuous analyte monitoring. Commercially available implantable glucose sensors generally employ electrodes fabricated on a planar substrate or wire electrodes. In either configuration the electrode surface is coated with an enzyme which is then further coated with a polymer membrane to control the amount of glucose and oxygen that reaches the electrode surface. In some glucose sensors the polymer membrane is hydrophilic which allows glucose to easily diffuse through the membrane layer. However, oxygen supply within the sensor can be an issue with some sensor designs. If insufficient oxygen is supplied within the sensor the lack of oxygen on the electrode surface can become an issue because the glucose sensor works by using the enzyme to catalyze a reaction between glucose and oxygen resulting in hydrogen peroxide that is oxidized at a working electrode. Only if there is an abundance of oxygen present at the working electrode, will the glucose measured by the electrode be proportional to the amount of glucose that reacts with the enzyme. Otherwise, in instances where insufficient oxygen is present at the working electrode, the glucose measurement is proportional to the oxygen concentration rather than the glucose concentration.

Further exacerbating the problem is the deficiency of oxygen relative to glucose in the human body. The ratio of glucose to oxygen in the human body ranges from approximately 10-to-1 to 1000-to-1. This typically means the enzyme catalyzed reaction at the working electrode is generally operating in a condition of oxygen deficiency which can result in many critical problems that influence accuracy, sensitivity and long-term reliability of in vivo sensors. Various approaches have been implemented to counteract the oxygen deficiency problem and increase the relative concentration of available oxygen at the electrode. For example, commercially available glucose sensor systems rely on a highly specialized glucose limiting membrane (GLM) rather than the simply hydrophilic membrane discussed above. Multiple commercial approaches have GLMs that are heterogeneous membranes with both hydrophobic and hydrophilic regions to draw in oxygen while also drawing in glucose. One drawback to the implementation of GLMs is the increased cost of the sensor due to the increased cost to manufacture the complex GLMs. Furthermore, material variability within the GLM and non-uniform dispersion of the hydrophilic areas often result in batch to batch variability that affects accuracy, sensitivity and reliability of the sensor.

Another drawback associated with the use of GLM is that effectiveness of a sensor may be adversely affected if metabolically active cells associated with insertion site trauma or host response interferes with or blocks a portion of the GLM. For example, if red blood cells were to pool in close proximity to the GLM flow of glucose and oxygen to the sensor electrode could be significantly impeded. Similarly, if white blood cells obstructed flow of glucose across the hydrophilic areas of a GLM the sensor electrode would output erroneous data because glucose that should otherwise reach the working electrode is being consumed by the white blood cells and there is no alternative path for glucose to diffuse to the working electrode.

Another drawback is the use of GLM can at least partially explain prolonged hydration and conditioning time for glucose sensors. Hydration and conditioning of the sensor requires transportation of fluid to the working electrode. However, because GLM favors the transport of oxygen, the hydrophobic regions of the GLM are placed over the electrode to promote diffusion of oxygen to the electrode. Being hydrophobic, those same areas repel water that is necessary to hydrate the sensor and transport the glucose to the electrode.

The previously discussed limitations of limiting membranes like GLM are exacerbated when attempting to measure multiple analytes using a single sensor. The inclusion or requirement of multiple limiting membranes can introduce complexity during the manufacturing process. Additionally, there may be additional complexity introduced by potential crosstalk between the different analytes being measured.

What is needed are real time in vivo sensing devices capable of monitoring multiple analytes within subjects within simplified manufacturing and reduced likelihood of crosstalk. Moreover, what is needed is the ability to monitor multiple analytes without the use or reliance on limiting membranes.

BRIEF SUMMARY OF THE INVENTION

In one embodiment an electrochemical sensor is disclosed that includes a first conductive substrate that is coupled to, and electrically isolated from, a second conductive substrate. The electrochemical sensor further includes a first electrode trace that is formed from the first conductive substrate and has at least one first electrode opening. Also included is a second electrode trace that is formed from the first conductive substrate that has at least one second electrode opening. A third electrode trace is also included that is formed from the second conductive substrate that includes at least one third electrode opening. The electrochemical sensor further includes a first transport material disposed as a barrier between any of the first, second or third electrode opening, wherein the first transport material is impervious to any byproduct of a reaction at any of the first, second or third electrode openings.

In another embodiment a multi-analyte electrochemical sensor is disclosed that includes a first conductive substrate that is coupled to, and electrically isolated from, a second conductive substrate. The multi-analyte electrochemical sensor includes a first electrode trace formed from the first conductive substrate and includes a plurality of first working electrode openings being formed in an A-side insulator. The electrochemical sensor also includes a second electrode trace formed from the first conductive substrate that includes a plurality of second working electrode openings being formed in the A-side insulator. Additionally included is a first transport material that covers the plurality of first working electrode openings along with a second transport material that covers the plurality of second working electrode openings. Further included is a third transport material that covers the first transport material and the second transport material. Where the third transport material forms a barrier between the first transport material and the second transport material. The sensor additionally includes a counter-reference electrode that is formed on the second conductive substrate.

Other features and advantages of the invention will become apparent from the following detailed description, taken in conjunction with the accompanying drawings that illustrate, by way of example, various features of embodiments of the invention.

BRIEF DESCRIPTION OF THE DRAWINGS

FIGS. 1A and 1B are an exemplary top view and a bottom view, respectively, of a sensor having multiple electrodes, in accordance with embodiments of the present invention.

FIGS. 3A and 3B are an exemplary illustration of an A-side and a B-side of a sensor, in accordance with another embodiment of the present invention.

FIGS. 4A and 4B are an exemplary illustration of an A-side and a B-side of a sensor, in accordance with another embodiment of the present invention.

FIGS. 5A and 5B are an exemplary illustration of an A-side and a B-side of a sensor, in accordance with another embodiment of the present invention.

FIGS. 6A and 6B are an exemplary illustration of an A-side and a B-side of a sensor, in accordance with another embodiment of the present invention.

DETAILED DESCRIPTION

Figure 2A:
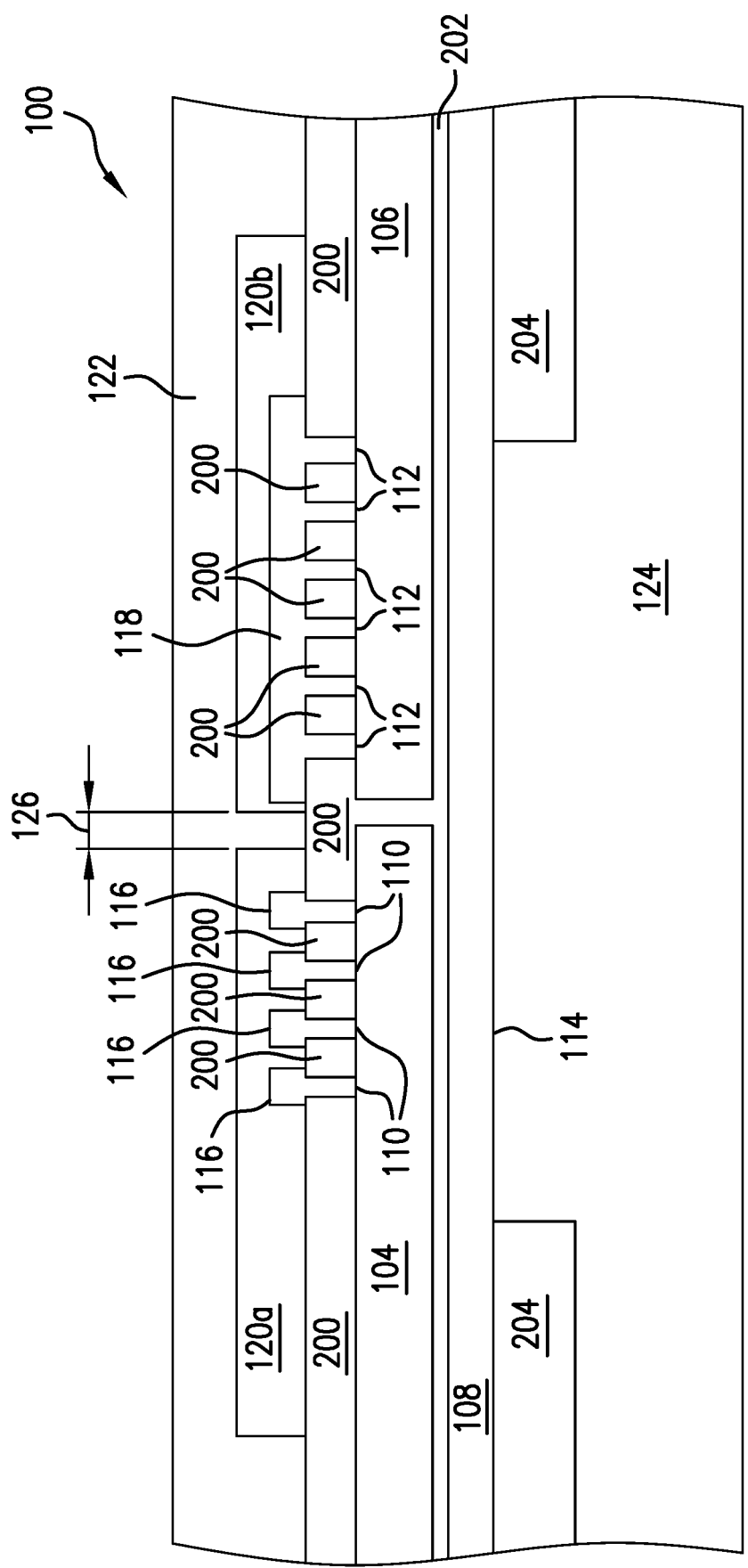
FIGS. 2A and 2B are exemplary cross-sectional illustrations of a portion of the sensor, in accordance with embodiments of the present invention.

Simultaneous continuous or periodic measurement of multiple analytes or chemical entities can enable measuring and monitoring of overall health and in particular, metabolic health. In addition to overall health and metabolic health, simultaneous measuring and monitoring of multiple analytes can further enable monitoring of disease progression or inflection that can further enable early clinical intervention for a multitude of disease states or conditions. The design of such medical monitoring systems requires an understanding of the pathophysiological processes associated with a particular illness or disease. From this basic understanding, a number of small molecules, biological markers of disease, and physiological measures with high diagnostic and prognostic value for a particular disease and/or condition can be identified. Sensors configured to detect and quantify concentrations of analytes or chemicals of interest can be functionalized to directly or indirectly measure the small molecules, biological markers, and associated with overall health, metabolic health, exposure to specific chemicals or a specific disease.

Advanced manufacturing techniques can then be used to integrate the sensors into a multi-analyte that can be deployed within a target population. Software algorithms that combine an understanding of general health, metabolic health, disease progression, artificial intelligence, and machine learning can be embedded in the instrumentation or systems that power and acquire data from a multi-parameter or multi-analyte sensor to record, report or assess the cellular and/or systemic progression of condition or disease. Configurable alerts and alarms associated with the medical monitoring system can be communicated through wired and wireless methods to enable general health monitoring or timely therapeutic intervention in order to derive the benefits of proactive disease or illness management.

Disclosed below is a robust sensor that enables real-time simultaneous continuous monitoring of multiple metrics or analytes that can be associated with general health, metabolic health, exposure to specific chemicals and detection and progression of various disease or illness states. Non-limiting exemplary analytes or compounds that can be detected or measured include, but are not limited to glucose, lactate, tissue oxygen concentration, ketones, choline, and the like.

In many embodiments, additional features or elements can be included or added to the exemplary features described below. Alternatively, in other embodiments, fewer features or elements can be included or removed from the exemplary features described below. In still other embodiments, where possible, combination of elements or features discussed or disclosed incongruously may be combined together in a single embodiment rather than discreetly as in the exemplary discussion. Accordingly, while the description below refers to particular embodiments of the invention, it will be understood that many modifications or combinations of the disclosed embodiments may be made without departing from the spirit thereof. The presently disclosed embodiments are therefore to be considered in all respects as illustrative and not restrictive.

FIGS. 1A and 1B are an exemplary top view and a bottom view, respectively, of a sensor 100 having multiple electrodes, in accordance with embodiments of the present invention. FIG. 1A is an exemplary illustration of an A-side 102a of the sensor 100. The sensor 100 includes a first electrode trace 106 and a second electrode trace 104. In preferred embodiments, the first and second electrode traces 106 and 104 are formed from a first substrate. In some embodiments the first substrate is a conductive material such as, but not limited to metals and carbon paste. Preferred exemplary metals include, but are not limited to, copper, silver, gold, and stainless steel. Exemplary, non-limiting techniques that can be used to form the first electrode trace 106 and the second electrode trace 104 from a single first substrate include removing material from a solid first substrate via photolithography or machining. Alternatively, additive techniques such as electrochemical deposition and additive manufacturing may also be used to form the first and second electrode traces 106 and 104.

The first electrode trace 106 includes a maximum first electrode height 106-$h1$ and a minimum first electrode height 106-$h2$. The second electrode trace 104 includes a second electrode height 104-$h$. Though not illustrated, in other embodiments it should be understood that the second electrode trace 104 may have varying heights as illustrated with the first electrode trace 106. Similarly, both the first electrode trace 106 and the second electrode trace 104 may have two or more heights that may be necessary to accommodate additional electrode traces on the sensor 100. The term "height" used above should be construed as relative regarding orientation and may be used interchangeably with the term "width". Alternatively, the term height may also be used interchangeably with a term such as, but not limited to, "dimension".

The first electrode trace 106 includes a plurality of first electrode openings 112 that are located toward a distal end 132 (FIG. 1B). Similarly, the second electrode trace 104 includes a plurality of second electrode openings 110 that are located toward a proximal end 134 (FIG. 1B). In FIG. 1A the first electrode openings 112 are substantially oriented along or upon a centerline 128 while the second electrode openings 110 are offset from the centerline 128. In many embodiments both the plurality of first electrode openings 112 and the second plurality of electrode opening 110 are openings in an electrical insulation layer applied over both the first and second electrode traces 104 and 106. The substantially circular shape of the first and second plurality of electrode openings 112 and 110 is intended to be illustrative and should not be construed as limiting. Furthermore, the use of multiple electrode openings on the first and second electrode traces 106 and 104 should also be construed as illustrative rather than limiting. In many embodiments either or both the first or second electrode traces 106 and 104 can have a single electrode opening rather than the plurality of openings as illustrated in FIGS. 1A and 1B. Likewise, the shape of any single electrode opening or each electrode opening of a plurality of electrode openings may have alternate shapes (e.g., polygons, ovoids, ellipses or combinations thereof, etc.) than those illustrated in FIG. 1A. Moreover, the relative position of the first electrode openings 112 and the second electrode openings 110 being upon, along, or offset from, the centerline 128 should not be construed as limiting. In various embodiments either the first electrode openings 112 or second electrode openings 110 could be configured to be on or off the centerline 128

A first reactive chemistry 118 is applied over a portion of the first electrode trace 106. As illustrated, the first reactive chemistry 118 is also applied over the first electrode openings 112. In many embodiments the first reactive chemistry 118 is applied having a width 118-$w$ and a height 118-$h$. In some embodiments, the height 118-$h$ is less than the maximum first electrode height 106-$h1$. In other embodiments, the height 118-$h$ is greater than the maximum first electrode height 106-$h1$. As illustrated in FIG. 1A, the first reactive chemistry 118 is applied contiguously across the plurality of first electrode openings 112.

A second reactive chemistry 116 is applied over the plurality of second electrode openings 110. In contrast to the contiguous application of the first reactive chemistry 118, the second reactive chemistry 116 is applied discreetly over each of the plurality of second electrode openings 110. As illustrated in FIG. 1A, the discrete application of the second reactive chemistry 116 results in the second reactive chemistry 116 having a diameter 116-$d$. The circular shape of the second reactive chemistry 116 should not be construed as limiting. In some embodiments the second reactive chemistry 116 has a different shape than the second electrode opening 110. For example, in some embodiments the plurality of second electrode opening 110 may be circular while the second reactive chemistry 116 has a shape of a polygon, ovoid, elliptical, or combination thereof.

Returning to the circular embodiment of reactive chemistry 116 in FIG. 1A, in some embodiments the diameter 116-$d$ is smaller than the second electrode opening 110. In other embodiments, the diameter 116-$d$ is equal to the second electrode opening 110. In still other embodiments, the diameter 116-$d$ is greater than the second electrode opening 110. Furthermore, in still additional embodiments, the diameter 116-$d$ is greater than the second electrode trace height 104-$h$. In embodiments where the second reactive chemistry 116 is a different shape than the second electrode opening 110, the dimensions of the different shape second reactive chemistry 116 may also be smaller, substantially similar to, or larger than the second electrode opening 110 or even larger than second electrode trace height 104-$h$.

The illustration of the first reactive chemistry 118 being applied in a contiguous manner over the plurality of first electrode openings 112 should not be construed as limiting. In some embodiments the first reactive chemistry 118 may be applied discretely over the first electrode openings 112 in a manner similar to how the second reactive chemistry 116 is applied over the second electrode openings 110. Similarly, in various other embodiments, the second reactive chemistry 116 may be applied contiguously over the second electrode openings 110 in a manner similar to the first reactive chemistry 118 over the first electrode openings 112. In still other embodiments, both the first and second reactive chemistries 118 and 116 may be applied contiguously over both the first and second electrode openings 112 and 110. Moreover, in additional embodiments, various combinations of contiguous and/or discrete applications of first or second reactive chemistries 118 and 116 over individual or combinations of their respective electrode openings are contemplated in order to tune or optimize sensor performance characteristics such as, but not limited to sensitivity of the sensor to detect an analyte of interest, the duration of time the sensor functions to measure an analyte or analytes of interest and the like.

In various embodiments, non-limiting examples of the first reactive chemistry 118 and the second reactive chemistry 116 includes oxidase enzymes such as, but not limited to glucose oxidase, lactate oxidase, and choline oxidase. In still other embodiments, additional non-limiting examples of a first and second reactive chemistry 118 and 116 include dehydrogenase enzymes such as, but not limited to glucose dehydrogenase, lactate dehydrogenase and 3-hydroxybutyrate dehydrogenase. In still other embodiments, either or both the first reactive chemistry 118 and the second reactive chemistry 116 may be optionally omitted thereby enabling each respective electrode to electrochemically detect tissue oxygen or other reactive oxygen species. The specific examples discussed regarding the first reactive chemistry should not be construed as definitive or limiting. Rather, it should be understood that additional or alternative reactants may be incorporated within the first and second reactive chemistry to electrochemically detect desired analytes, compounds or molecules of interest.

The sensor 100 further includes a first transport material 120$b$ that is selectively applied over a portion of the first electrode trace 106. As illustrated in FIG. 1A, the first transport material 120$b$ is applied over both the first electrode openings 112 and the first reactive chemistry 118. Similarly, a second transport material 120$a$ is selectively applied over a portion of the second electrode trace 104. The application of the second transport material 120a further covers the second electrode openings 110 and the second reactive chemistry 116.

In non-limiting exemplary embodiments, the first transport material 120b and the second transport material 120a are hydrogel materials that freely enable transport of an entirety of fluid that surrounds the sensor 100 after it is placed subdermally. In embodiments where the sensor 100 is placed in subcutaneous tissue the sensor 100 is surrounded by interstitial fluid. In these embodiments, the first and second transport materials 120a and 120b are intended to enable interstitial fluid, and everything it contains, to freely move unimpeded throughout the respective transport materials. Furthermore, the first transport material 120b and the second transport material are selected to further enable unencumbered transport of reactants and byproducts of electrochemical reactions between analytes, compounds and molecules within interstitial fluid and either of the first and second reactive chemistries 118 and 116. Exemplary compounds, molecules, reactants and byproducts that are intended to be free transmissible via either the first and second transport materials 120b and 120a include, but are not limited to glucose, lactate, ketones, choline, acetylcholine, oxygen, hydrogen peroxide and the like.

The first transport material 120b and the second transport material 102a are physically separated from each other by a gap 126. The gap 126 may also be referred to as a barrier, and the gap 126 or the barrier 126 is intended to prevent or reduce the likelihood of crosstalk from the migration or transport of compounds, analytes, reactants, and by-products of chemical or electrochemical reactions generated by the reaction between the respective reactive chemistries and the analytes/compounds of interest. For example, In embodiments where both reactive chemistries 118 and 116 include oxidase based enzymes, the barrier 126 is intended to prevent migration of by-products of the oxidase reaction (e.g., hydrogen peroxide) from the first electrode openings 112 to the second electrode openings 110 and vice versa.

The sensor 100 further includes a third transport material 122 that is applied at least over a portion of the first electrode trace 106 and at least a portion of the second electrode trace 104. The third transport material 122 further covers the first and second electrode openings 112 and 110. Moreover, the third transport material 122 is applied over the barrier 126. Additionally, the third transport material 122 also covers the first and second reactive chemistries 118 and 116. In FIG. 1A, the third transport material 122 is applied within or inside an edge 130 for the sensor 100. In other embodiments, the third transport material 122 is applied to, or over the edge 130.

The third transport material 122 is intended to prevent transmission of analytes, compounds or molecules of interest. Accordingly, in some embodiments, the third transport material is hydrophobic. In many embodiments, the third transport material 122 is at least substantially impermeable to liquids. In addition to being hydrophobic or impermeable to liquids, another quality that is desirable for many embodiments of the third transport material 122 is that it is gas permeable. A non-limiting example of a third transport material 122 is silicone or a compound containing silicone. The specific example of a third transport material 122 should not be construed as limiting. Other compounds or materials that are hydrophobic or prevent transport or transmission of analytes of interest while being gas permeable should be understood to be contemplated by this disclosure.

FIG. 1B is an exemplary top view of a B-side 102b of the sensor 100. The B-side 102b includes a third electrode trace 108 formed from a second substrate. The second substrate is electrically isolated from the first and second electrode traces 106 and 104 (FIG. 1A) formed from the first substrate. The second substrate is an electrically conductive material that may be the same or different material from the first substrate. A third electrode opening 114 is formed on the third electrode trace 108. The third electrode opening 114 has a height 114-h and a width 114-w. A fourth transport material 124 that is applied over at least a portion of the third electrode trace 108 and the third electrode opening 114. In some embodiments, the fourth transport material 124 is similar or identical to either the first or second transport materials 120b or 120a.

Viewing FIGS. 1A and 1B together, the sensor 100 includes two working electrodes and a single combined counter/reference electrode (alternatively, a pseudo-reference electrode). The first working electrode is located, or formed, on the first electrode trace 106 and the second working electrode is located, or formed on the second electrode trace 104. The counter/reference electrode is formed on the third electrode trace 108.

In alternative embodiments, viewing FIGS. 1A and 1B together, the sensor 100 includes a single working electrode, a counter electrode and a reference electrode. In this alternative embodiment, the working electrode is located, or formed on the first electrode trace 106. The counter electrode and the reference electrode may be formed on either the second electrode trace 104 or the third electrode trace 108. As would be understood by one skilled in the art, the use of a three electrode system may necessitate the removal or deletion of the second reactive chemistry thereby making the sensor capable of detecting a single analyte. However, as discussed above, additional electrode traces and corresponding working electrodes can be formed from either the first or second substrate to further enable multi-analyte measurements with a shared counter electrode and a shared reference electrode.

In still other embodiments, multiple counter electrodes and multiple reference electrodes may be formed on either the first or second substrate to enable each working electrode to include its own counter electrode and reference electrode. This embodiment can alternatively be viewed as a multiple analyte sensor where each analyte is detected using a three electrode (working, counter and reference electrode) system. In still other embodiments, multiple combined counter/reference electrodes can be formed on either the first or second substrate to enable each working electrode to have an independent counter/reference electrode. This embodiment can alternatively be viewed as a multiple analyte sensor where each analyte is detected using a two electrode (working and combined counter/reference) system.

Figure 2B:
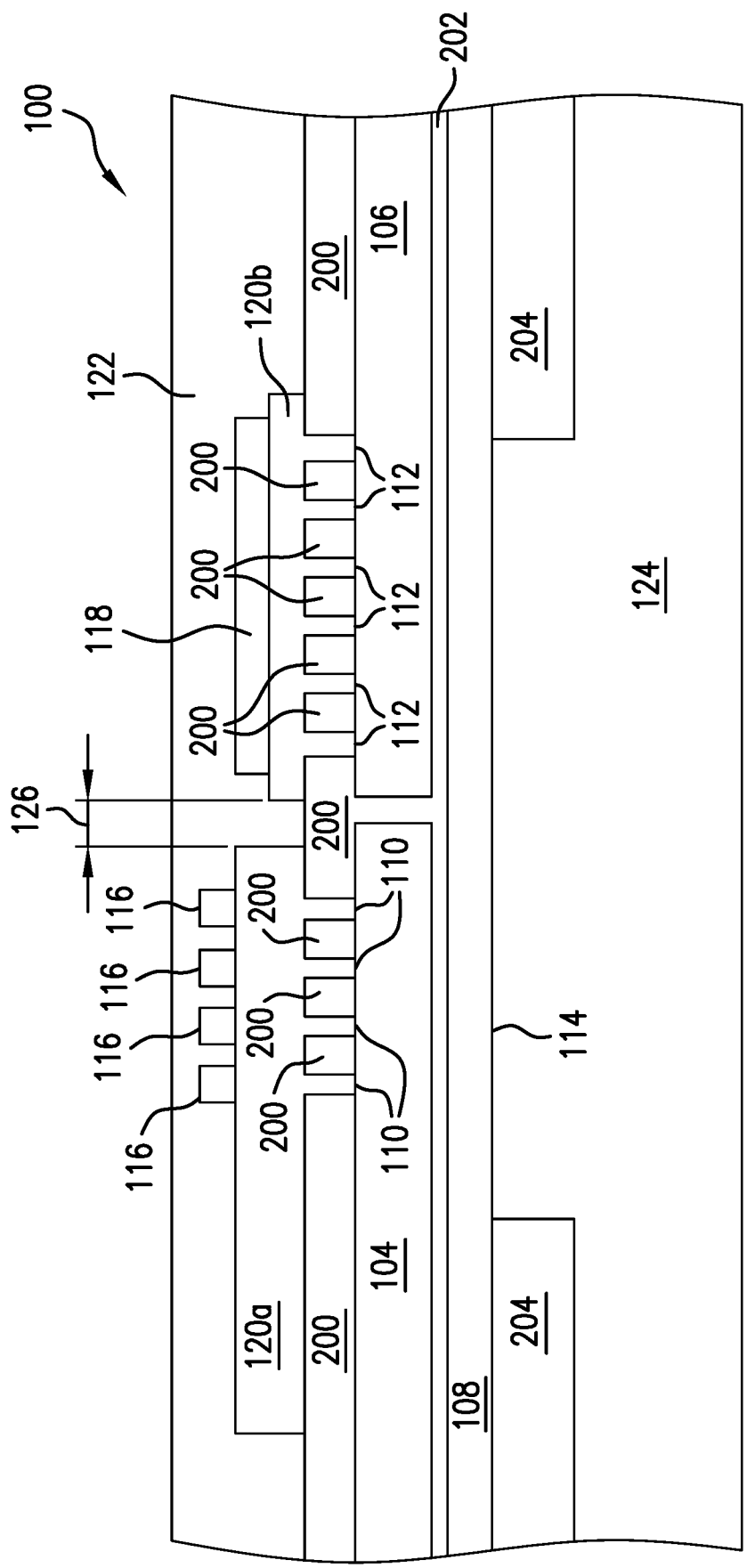

FIGS. 2A and 2B are exemplary cross-sectional illustrations of a portion of the sensor 100, in accordance with embodiments of the present invention. FIGS. 2A and 2B should not be construed as being to-scale and accordingly, the relative thicknesses of each layer of the cross-section is purely for illustrative purposes. It should further be noted that the cross-sections represented in FIGS. 2A and 2B are intended to represent a view that jogs or switches between the first electrode openings 112 and the second electrode openings 110.

FIGS. 2A and 2B enable visualization of insulation 200, 202 and 204 within the sensor 100. Insulation 202 electrically isolates the first and second electrode traces 106 and 104 from the third electrode trace 108. Additionally, first and second electrode openings 112 and 110 are illustrated as openings in the insulation 200 that directly covers both the first and second electrode traces 106 and 104. Third electrode opening 114 is illustrated as an opening in the insulation 204 that directly covers the third electrode trace 108.

In FIG. 2A, the first and second reactive chemistries 118 and 116 are applied directly over the insulation 200 and accordingly fill the first and second electrode openings 112 and 110. This places the first and second reactive chemistries 118 and 116 directly in contact with the respective first and second electrode traces 106 and 104. In many embodiments, the first and second electrode traces 106 and 104 undergo surface preparation such as electroplating and the like and it should be understood that in those embodiments, the respective reactive chemistries will be in contact with the prepared surfaces of the respective electrode trace.

In FIG. 2A, the first transport material 120b is applied over both the first reactive chemistry 118 and the first electrode openings 112. Note that the first transport material 120b is in direct contact with the first reactive chemistry 118 but is not directly in contact with the first electrode openings 112. Similarly, the second transport material 120a is applied over both the second reactive chemistry 116 and the second electrode openings 110. Again, note that the second transport material 120b is in direct contact with the second reactive chemistry 116 but is not directly in contact with the second electrode openings 112. Additionally, note the inclusion of barrier 126 between the first and second transport materials 120b and 120a. The third transport material 122 is applied directly over the first and second transport materials 120b and 120a. Additionally, the third transport material 122 fills the gap 126 (alternatively, the barrier 126). Accordingly, the barrier 126 includes physical separation between the first transport material 120b and the second transport material 120a. Moreover, the physical separation is augmented by a physical barrier made of the third transport material 122 that, as discussed above, is impervious to liquids and transmission of some analytes, compounds and electrochemical byproducts.

In FIG. 2B the first transport material 120b is applied directly over the insulation 200 and fills the first electrode openings 112. Similarly, the second transport material 120a is applied directly over the insulation 200 and fills the second electrode openings 110. The first reactive chemistry 118 is contiguously applied over both the insulation 200, the first electrode openings 112, and the first transport material 120b. The second reactive chemistry 116 is discreetly, or non-contiguously applied over the insulation 200, the second electrode openings 110, and the second transport material 120a. Note that in FIG. 2B, the first transport material 120b is in direct contact with the first electrode openings and the first reactive chemistry 118. Likewise, the second transport material 120b is in direct contact with the second electrode openings and the second reactive chemistry 120a. Alternatively, it can be viewed as the first reactive chemistry is not in contact with the first electrode trace and the second reactive chemistry is not in contact with the second electrode trace.

The barrier 126 is located between the first and second transport materials 120b and 120a. The third transport material 122 is applied directly over the first and second transport materials 120b and 120a along with the first and second reactive chemistries 118 and 116. Note that in FIG. 2B the first and second reactive chemistries 118 and 116 are directly in contact with the third transport material 122. Additionally, the third transport material 122 fills the gap 126 (alternatively, the barrier 126). Accordingly, the barrier 126 includes physical separation between the first transport material 120b and the second transport material 120a. Also, the barrier 126 physically separates the first reactive chemistry 118 and the second reactive chemistry 116. Moreover, the physical separation is augmented by a physical barrier made of the third transport material 122 that, as discussed above, is impervious to liquids and transmission of many analytes, compounds and electrochemical byproducts. FIGS. 2A and 2B also illustrate the contiguous application of the first reactive chemistry 118 and the discrete, or discontiguous application of the second reactive chemistry 116.

Though FIGS. 2A and 2B illustrate each sensor 100 having both the first and second electrodes being formed either with reactive chemistry in contact with electrode openings or not having reactive chemistry in contact with electrode openings, the different embodiments in FIGS. 2A and 2B may be combined on a single sensor. For example, In some embodiments, the first electrode is formed with the first reactive chemistry being in direct contact with the first electrode opening (as shown in FIG. 2A) and the second electrode is formed with the second reactive chemistry being over, but not in direct contact with the second electrode openings (as shown in FIG. 2B). In such an embodiment, the barrier 126 remains, along with the third transport material 122 filling in the barrier 126.

FIGS. 3A and 3B are an exemplary illustration of A-side 102a and B-side 102b of a sensor 301, in accordance with another embodiment of the present invention. FIG. 3A is an illustration of A-side 102a of a sensor 301 where the first electrode trace 106 supports a first working electrode and the third electrode trace 108 supports a first counter/reference electrode. In this embodiment, the A-side 102a includes the first electrode trace 106 that further includes first electrode openings 112 located substantially on the centerline 128 of the distal end 132. The first reactive chemistry 118 is applied discreetly over each of the first electrode openings 112. Note that as illustrated, the first reactive chemistry 118 has a different shape than the first electrode openings 112. Additionally, the first transport material 120b is applied over both the first electrode openings 112 and at least a portion of the first electrode trace 106. Third transport material 122 is placed over a portion of the first electrode trace 106, the first electrode openings 112, and the first reactive chemistry 118 and the first transport material 120b. In many embodiments the third transport material 122 is a material that includes silicone.

In some embodiments, the first reactive chemistry 118 is placed directly in contact with the first electrode openings 112 as illustrated in FIG. 2A. In other embodiments, the first reactive chemistry 118 is not placed directly in contact with the first electrode openings 112 as illustrated in FIG. 2B. In still other embodiments, a portion of the first electrode openings 112 are directly in contact with first reactive chemistry 118 and the remainder of the first electrode openings 112 are not in direct contact with the first reactive chemistry 118. Co-located on A-side 102a, toward the proximal end 134 is third electrode trace 108 having third electrode opening 114. Covering at least a portion of the third electrode trace 108 and the third electrode opening 114 is fourth transport material 124. In some embodiments, the fourth transport material 124 is the same as the first transport material 120b. In many of these embodiments, that can be understood as the first and fourth transport materials 120b and 124 being a non-restrictive hydrogel. In other embodiments, the fourth transport material 124 is the same as the third transport material 122. In these embodiments, the gap 126 is filled and minimizes or prevents crosstalk between the first and third electrode traces 106 and 108.

FIG. 3B is an illustration of B-side 102*b* of a sensor 301 where the second electrode trace 104 supports a second working electrode and a fourth electrode trace 300 supports a second counter/reference electrode. In this embodiment, the B-side 102*b* includes the second electrode trace 104 that further includes second electrode openings 110 located substantially on the centerline 128 of the distal end 132. The second reactive chemistry 116 is applied contiguously over the second electrode openings 110. Additionally, the second transport material 120*a* is applied over at least a portion of the second electrode trace 104 along with the second electrode openings 110. Third transport material 122 is placed over at least a portion of the second electrode trace 104, the second electrode openings 110, the second reactive chemistry 116 and the second transport material 120*a*. Co-located on B-side 102*b*, toward the proximal end 134 is fourth electrode trace 300 having fourth electrode opening 302. Covering at least a portion of the fourth electrode trace 300 and the fourth electrode opening 302 is fifth transport material 304. In many embodiments, the fifth transport material 304 is identical or substantially similar to fourth transport material 124.

In FIGS. 3A and 3B, the first working electrode is on A-side 102*a* and the second working electrode is on B-side 102*b*. Both the first and second working electrodes are substantially located along the centerline 128 toward the distal end 132. Being substantially co-located on opposite sides of the sensor 301 ensures that both the first and second working electrodes are inserted to substantially the same depth. Accordingly, any fluid surrounding the sensor 301 should be substantially the same. This is different from the embodiment illustrated in FIG. 1A, where the first electrode is formed near the distal end and the second electrode is formed at a distance further from the distal end.

FIGS. 4A and 4B are an exemplary illustration of A-side 102*a* and B-side 102*b* of a sensor 400, in accordance with another embodiment of the present invention. FIG. 4A is an illustration of A-side 102*a* of the sensor 400 where the first electrode trace 106 supports a counter/reference electrode and the second electrode trace 104 supports a working electrode. In this embodiment, the A-side 102*a* includes the first electrode trace 106 that further includes first electrode openings 112 located substantially on the centerline 128. The first transport material 120*b* is applied over both the first electrode openings 112 and at least a portion of the first electrode trace 106.

FIG. 4B is an illustration of B-side 102*b* of the sensor 400 where the second electrode trace 104 supports a first working electrode. In this embodiment, the B-side 102*b* includes the second electrode trace 104 that further includes second electrode openings 110 located substantially on the centerline 128 of the distal end 132. The second reactive chemistry 116 is applied discretely over each of the second electrode openings 110. Additionally, the second transport material 120*a* is applied over at least a portion of the second electrode trace 104 along with the second electrode openings 110. Third transport material 122 is placed over at least a portion of the second electrode trace 104, the second electrode openings 110, the second reactive chemistry 116 and the second transport material 120*a*.

FIGS. 5A and 5B are an exemplary illustration of A-side 102*a* and B-side 102*b* of a sensor 500, in accordance with another embodiment of the present invention. FIG. 5A is an illustration of A-side 102*a* of the sensor 500 where the third electrode trace 108 supports a first counter/reference electrode and the fourth electrode trace 300 supports a second counter/reference electrode. In this embodiment, the A-side 102*a* includes the third electrode trace 108 that further includes third electrode opening 114 located substantially on the centerline 128 toward the distal end 132. The fourth transport material 124 is applied over both the third electrode opening 114 and at least a portion of the third electrode trace 108.

Co-located on the A-side 102*a* is fourth electrode trace 300 that further includes fourth electrode opening 302 that is offset from the centerline 128 toward the proximal end 134. The fifth transport material 304 is applied over both the fourth electrode opening 302 and at least a portion of the fourth electrode trace 300.

FIG. 5B is an illustration of B-side 102*b* of the sensor 500 where first electrode trace 106 supports a first working electrode and the second electrode trace 104 supports a second working electrode. In this embodiment, the B-side 102*b* includes the first electrode trace 106 that further includes first electrode openings 112 located substantially on the centerline 128 of the distal end 132. The first reactive chemistry 118 is applied discretely over each of the first electrode openings 112. Additionally, the first transport material 120*b* is applied over at least a portion of the first electrode trace 106 and the first electrode openings 112.

Co-located on the B-side 102*b* is the second electrode trace 104 that further includes the second electrode opening 110 that is offset from the centerline 128 toward the proximal end 134. The second reactive chemistry 116 is applied substantially coincident over the second electrode opening 110. Additionally, the second transport material 120*a* is applied over at least a portion of the second electrode trace 106 and the second electrode opening 110. Third transport material 122 is placed over at least a portion of the first and second electrode trace 106 and 104, the first electrode openings 112, the second electrode opening 110, the first and second reactive chemistries 118 and 116 and the first and second transport material 120*b* and 120*a*.

FIGS. 6A and 6B are an exemplary illustration of A-side 102*a* and B-side 102*b* of a sensor 601, in accordance with another embodiment of the present invention. FIG. 6A is an illustration of A-side 102*a* of the sensor 601 where the first electrode trace 106 supports a first working electrode and the third electrode trace 108 supports a first counter/reference electrode. In this embodiment, the A-side 102*a* includes the first electrode trace 106 that further includes first electrode openings 112 toward the distal end 132 and are also offset from the centerline 128. The first reactive chemistry 118 is applied contiguously over all of the first electrode openings 112 and at least a portion of the first electrode trace 106. Additionally, the first transport material 120*b* is applied over at least a portion of the first electrode trace 106 and the first electrode openings 112.

Co-located on the A-side 102*a* is the third electrode trace 108 that further includes third electrode opening 114 located offset from the centerline 128 toward the proximal end 132. The fourth transport material 124 is applied over both the third electrode opening 114 and at least a portion of the third electrode trace 108.

FIG. 6B is an illustration of B-side 102*b* of the sensor 601 where second electrode trace 104 supports a second working electrode, the fourth electrode trace 300 supports a second counter/reference electrode and a fifth electrode trace 604 supports a third working electrode. In this embodiment, the B-side 102*b* includes the second electrode trace 104 that further includes second electrode openings 110 that are offset from the centerline 128. The second reactive chemistry 116 is applied contiguously over each of the second electrode openings 110 and at least a portion of the second electrode conductor 104. Additionally, the second transport material 120*a* is applied over at least a portion of the second electrode trace 104 and the second electrode openings 110.

Co-located on the B-side 102*b* is the fourth electrode trace 300 that further includes the fourth electrode openings 302 that are substantially located on the centerline 128. Note that in this embodiment, the electrode openings 302 open over a height that is greater than the height of the fourth electrode trace 300. The fifth transport material 304 is applied over both the fourth electrode openings 302 and at least a portion of the fourth electrode trace 300. Also co-located on the B-side 102*b* is the fifth electrode trace 604 that further includes fifth electrode openings 600 that are located substantially along centerline 128 toward the distal end 132. A third reactive chemistry 602 is applied contiguously over each of the fifth electrode openings 600 and at least a portion of the fifth electrode trace 604.

In many embodiments, additional features or elements can be included, added or substituted for some or all of the exemplary features described above. An exemplary, non-limiting example is the use of a three electrode system (working, counter and reference electrodes) where a two electrode system (working and combined counter/reference electrodes) are discussed above. Alternatively, in other embodiments, fewer features or elements can be included or removed from the exemplary features described above. In still other embodiments, where possible, combinations of elements or features discussed or disclosed incongruously may be combined together in a single embodiment rather than discreetly or in the specific combinations described in the exemplary description found above. Accordingly, while the description above refers to particular embodiments of the invention, it will be understood that many modifications or combinations of the disclosed embodiments may be made without departing from the spirit thereof. The presently disclosed embodiments are therefore to be considered in all respects as illustrative and not restrictive.

The invention claimed is:

1. A multi-analyte electrochemical sensor, comprising:
    a first conductive substrate being coupled to, and electrically isolated from, a second conductive substrate;
    a first electrode trace being formed from the first conductive substrate, the first electrode trace including a plurality of first working electrode openings being formed in an A-side insulator;
    a second electrode trace being formed from the first conductive substrate, the second electrode trace including a plurality of second working electrode openings being formed in the A-side insulator;
    a first transport material covering the plurality of first working electrode openings;
    a second transport material covering the plurality of second working electrode openings;
    a third transport material covering the first transport material and the second transport material, the third transport material forming a barrier between the first transport material and the second transport material, and
    a counter-reference electrode being formed on the second conductive substrate.

2. The multi-analyte electrochemical sensor of claim 1, further comprising:
    a first working electrode having a first reactive chemistry being contiguously deposited between the first transport material and the A-side insulator, the first reactive chemistry filling the first working electrode openings.

3. The multi-analyte electrochemical sensor of claim 2, further comprising:
    a second working electrode having a second reactive chemistry being discreetly deposited within each of the plurality of second electrode openings and the second transport material.

4. The multi-analyte electrochemical sensor of claim 3, wherein the second reactive chemistry fills each of the plurality of second electrode openings and is further deposited over the A-side insulator.

5. The multi-analyte electrochemical sensor of claim 3, wherein the barrier is impervious to reaction products generated by the first reactive chemistry and reaction products generated by the second reactive chemistry.

6. The multi-analyte electrochemical sensor of claim 5, wherein the first transport material is a hydrogel configured to enable transport of a first analyte to the first reactive chemistry.

7. The multi-analyte electrochemical sensor of claim 6, wherein the second transport material is a hydrogel configured to enable transport of a second analyte to the second reactive chemistry.

8. The multi-analyte electrochemical sensor of claim 7, wherein the third transport material is impervious to at least one of the first analyte or the second analyte.

9. The multi-analyte electrochemical sensor of claim 1, further comprising:
    a first working electrode having a first reactive chemistry being contiguously deposited on a top surface of the first transport material, the first reactive chemistry laterally overlapping the electrode openings.

10. The multi-analyte electrochemical sensor of claim 9, further comprising:
    a second working electrode having a second reactive chemistry being discreetly deposited within each of the plurality of second electrode openings and the second transport material.

* * * * *